(12) United States Patent
Altschul et al.

(10) Patent No.: US 8,865,693 B2
(45) Date of Patent: *Oct. 21, 2014

(54) PREVENTION OF INFECTION

(75) Inventors: Randice Lisa Altschul, Cliffside Park, NJ (US); Neil David Theise, New York, NY (US); Myron Rapkin, Indianapolis, IN (US); Rebecca O'Brien, Shell Knob, MO (US)

(73) Assignee: Pop Test Cortisol LLC, Cliffside Park, NJ (US)

( * ) Notice: Subject to any disclaimer, the term of this patent is extended or adjusted under 35 U.S.C. 154(b) by 172 days.

This patent is subject to a terminal disclaimer.

(21) Appl. No.: 13/432,174

(22) Filed: Mar. 28, 2012

(65) Prior Publication Data

US 2012/0253312 A1   Oct. 4, 2012

Related U.S. Application Data

(60) Provisional application No. 61/516,227, filed on Mar. 31, 2011.

(51) Int. Cl.
*A61K 31/56* (2006.01)
*A61K 31/33* (2006.01)
*A61K 31/573* (2006.01)

(52) U.S. Cl.
CPC ............... *A61K 31/56* (2013.01); *A61K 31/573* (2013.01)
USPC ........................................... 514/183; 514/182

(58) Field of Classification Search
CPC ............................. A61K 31/56; A61K 31/573
USPC ........................ 514/169, 172, 174, 182, 183
See application file for complete search history.

(56) References Cited

U.S. PATENT DOCUMENTS

| 6,011,025 | A | 1/2000 | Gebhard |
| 8,658,128 | B2 * | 2/2014 | Altschul et al. ............. 424/1.11 |
| 2012/0245552 | A1 * | 9/2012 | Altschul et al. ............. 604/403 |

FOREIGN PATENT DOCUMENTS

EP   0298020 A1   3/1987

* cited by examiner

*Primary Examiner* — My-Chau T Tran
(74) *Attorney, Agent, or Firm* — Arthur Jacob

(57) ABSTRACT

The invention relates to compounds and methods for the prevention and/or treatment of infection after stroke.

14 Claims, 7 Drawing Sheets

| | |
|---|---|
| PARTICIPANTS | Rosenzweig and co-workers |
| STUDY DESIGN | Prospective cohort |
| POSTSTROKE INTERVAL | Hospital admission (mean 37d) |
| NUMBER OF PATIENTS | 607 (91% ischaemic stroke) |
| TYPE OF INFECTION | Chest Infection |
| FREQUENCY OF INFECTION | 12% |
| TYPE OF INFECTION | Urinary tract infection |
| FREQUENCY OF INFECTION | 16% |
| PARTICIPANTS | Fassbender and co-workers |
| STUDY DESIGN | Prospective series |
| POSTSTROKE INTERVAL | 1w |
| NUMBER OF PATIENTS | 52 |
| TYPE OF INFECTION | Pneumonia |
| FREQUENCY OF INFECTION | 10% |
| TYPE OF INFECTION | Urinary tract infection |
| FREQUENCY OF INFECTION | 19% |
| TYPE OF INFECTION | Other |
| FREQUENCY OF INFECTION | 2% |
| PARTICIPANTS | Johhnston and co-workers |
| STUDY DESIGN | Prospective multicentre trial |
| POSTSTROKE INTERVAL | Trial duration (3 m) |
| NUMBER OF PATIENTS | 279 |
| TYPE OF INFECTION | Pneumonia |
| FREQUENCY OF INFECTION | 10% |

FIG. 1A

| | |
|---|---|
| TYPE OF INFECTION | Urinary tract infection |
| FREQUENCY OF INFECTION | 11% |
| TYPE OF INFECTION | Other |
| FREQUENCY OF INFECTION | 3% |
| PARTICIPANTS | Georgilis and co-workers |
| STUDY DESIGN | Retrospective series |
| POSTSTROKE INTERVAL | Hospital admission (duration not specified) |
| NUMBER OF PATIENTS | 330 (85% ischaemic stroke) |
| TYPE OF INFECTION | Respiratory tract infection |
| FREQUENCY OF INFECTION | 10% |
| TYPE OF INFECTION | Urinary tract infection |
| FREQUENCY OF INFECTION | 12% |
| TYPE OF INFECTION | Other |
| FREQUENCY OF INFECTION | 1% |
| PARTICIPANTS | Grau and co-workers |
| STUDY DESIGN | Prospective series |
| POSTSTROKE INTERVAL | 48 h |
| NUMBER OF PATIENTS | 119 |
| TYPE OF INFECTION | Respiratory tract infection |
| FREQUENCY OF INFECTION | 11% |
| TYPE OF INFECTION | Urinary tract infection |
| FREQUENCY OF INFECTION | 2% |
| TYPE OF INFECTION | Other |
| FREQUENCY OF INFECTION | 6% |
| PARTICIPANTS | Tirschwell and co-workers |

FIG. 1B

| | |
|---|---|
| STUDY DESIGN | Population-based hospital discharge database |
| POSTSTROKE INTERVAL | Hospital admission (mean 7-8 d) |
| NUMBER OF PATIENTS | 4757 |
| TYPE OF INFECTION | Pneumonia |
| FREQUENCY OF INFECTION | 7% |
| TYPE OF INFECTION | Urinary tract infection |
| FREQUENCY OF INFECTION | 9% |
| PARTICIPANTS | Langhorne and co-workers |
| STUDY DESIGN | Prospective cohort |
| POSTSTROKE INTERVAL | Hospital admission (mean-51d) |
| NUMBER OF PATIENTS | 311 (90% ischaemic stroke) |
| TYPE OF INFECTION | Chest infection |
| FREQUENCY OF INFECTION | 22% |
| TYPE OF INFECTION | Urinary tract infection |
| FREQUENCY OF INFECTION | 23% |
| TYPE OF INFECTION | Other |
| FREQUENCY OF INFECTION | 19% |
| PARTICIPANTS | Roth and co-workers |
| STUDY DESIGN | Consecutive series |
| POSTSTROKE INTERVAL | Mean interval 17-4±14-9 d |
| NUMBER OF PATIENTS | 1029 (71% ischaemic stroke) |
| TYPE OF INFECTION | Pneumonia |
| FREQUENCY OF INFECTION | 20% |
| PARTICIPANTS | Kammersgaard and co-workers |
| STUDY DESIGN | Prospective community based cohort |

FIG. 1C

| | |
|---|---|
| POSTSTROKE INTERVAL | 3d |
| NUMBER OF PATIENTS | 1156 (92% ischaemic stroke) |
| TYPE OF INFECTION | Any infection |
| FREQUENCY OF INFECTION | 19% |
| PARTICIPANTS | Weimar and co-workers |
| STUDY DESIGN | Prospective hospital-based registry |
| POSTSTROKE INTERVAL | 7d |
| NUMBER OF PATIENTS | 3866 |
| TYPE OF INFECTION | Pneumonia |
| FREQUENCY OF INFECTION | 7% |
| PARTICIPANTS | Hamidon and co-workers |
| STUDY DESIGN | Consecutive series |
| POSTSTROKE INTERVAL | 3d |
| NUMBER OF PATIENTS | 163 |
| TYPE OF INFECTION | Pneumonia |
| FREQUENCY OF INFECTION | 12% |
| TYPE OF INFECTION | Urinary tract infection |
| FREQUENCY OF INFECTION | 4% |
| PARTICIPANTS | Hilker and co-workers |
| STUDY DESIGN | Prospective series |
| POSTSTROKE INTERVAL | Intensive care unit admission (mean latency 1.8±1.9d) |
| NUMBER OF PATIENTS | 124 |
| TYPE OF INFECTION | Stroke-associated Pneumonia |
| FREQUENCY OF INFECTION | 21% |
| PARTICIPANTS | Katzan and co-workers |

FIG. 1D

| | |
|---|---|
| STUDY DESIGN | Population-based cohort |
| POSTSTROKE INTERVAL | Hospital admission (duration not specified) |
| NUMBER OF PATIENTS | 14 293 (subtypes not specified) |
| TYPE OF INFECTION | Pneumonia |
| FREQUENCY OF INFECTION | 7% |
| PARTICIPANTS | Pittock and co-workers |
| STUDY DESIGN | Consecutive series |
| POSTSTROKE INTERVAL | 2w |
| NUMBER OF PATIENTS | 106 (2-week survivors) |
| TYPE OF INFECTION | Respiratory tract infection |
| FREQUENCY OF INFECTION | 33% |
| PARTICIPANTS | Aslanyan and co-workers |
| STUDY DESIGN | Prospective intl. trial |
| POSTSTROKE INTERVAL | Trial duration (3 m) |
| NUMBER OF PATIENTS | 1455 |
| TYPE OF INFECTION | Pneumonia |
| FREQUENCY OF INFECTION | 14% |
| TYPE OF INFECTION | Urinary tract infection |
| FREQUENCY OF INFECTION | 17% |
| PARTICIPANTS | Ovbiagele and co-workers |
| STUDY DESIGN | Prospective stroke registry |
| POSTSTROKE INTERVAL | Hospital admission (duration not specified) |
| NUMBER OF PATIENTS | 663 |
| TYPE OF INFECTION | Pneumonia |
| FREQUENCY OF INFECTION | 10% |

FIG. 1E

| | |
|---|---|
| TYPE OF INFECTION | Urinary tract infection |
| FREQUENCY OF INFECTION | 13% |
| PARTICIPANTS | Ersoz and co-workers |
| STUDY DESIGN | Prospective series |
| POSTSTROKE INTERVAL | Mean interval 188±285 d |
| NUMBER OF PATIENTS | 82 |
| TYPE OF INFECTION | Symptomatic urinary tract infection |
| FREQUENCY OF INFECTION | 27% |
| PARTICIPANTS | Kwanand Hand |
| STUDY DESIGN | Prospective cohort 9% TIA) |
| POSTSTROKE INTERVAL | 5d |
| NUMBER OF PATIENTS | 439 (91% ischaemic stroke) |
| TYPE OF INFECTION | Pneumonia |
| FREQUENCY OF INFECTION | 10% |
| TYPE OF INFECTION | Urinary tract infection |
| FREQUENCY OF INFECTION | 7% |
| TYPE OF INFECTION | Other |
| FREQUENCY OF INFECTION | 2% |
| PARTICIPANTS | Vargas and co-workers |
| STUDY DESIGN | Prospective cohort |
| POSTSTROKE INTERVAL | Hospital admission (median 9 days) |
| NUMBER OF PATIENTS | 229 (82% ischaemic stroke) |
| TYPE OF INFECTION | Acute bronchial |
| FREQUENCY OF INFECTION | 17% |
| TYPE OF INFECTION | Pneumonia |

FIG. 1F

| | |
|---|---|
| FREQUENCY OF INFECTION | 1% |
| TYPE OF INFECTION | Urinary tract infection |
| FREQUENCY OF INFECTION | 6% |
| TYPE OF INFECTION | Other |
| FREQUENCY OF INFECTION | 4% |
| PARTICIPANTS | Walter and co-workers |
| STUDY DESIGN | Prospective series |
| POSTSTROKE INTERVAL | Intensive care unit admission (mean latency 20±2-9 d) |
| NUMBER OF PATIENTS | 236 |
| TYPE OF INFECTION | Stroke-associated pneumonia |
| FREQUENCY OF INFECTION | 22% |
| PARTICIPANTS | Wong and co-workers |
| STUDY DESIGN | Prospective series |
| POSTSTROKE INTERVAL | 48 h |
| NUMBER OF PATIENTS | 156 |
| TYPE OF INFECTION | Pneumonia |
| FREQUENCY OF INFECTION | 1% |
| TYPE OF INFECTION | Urinary tract infection |
| FREQUENCY OF INFECTION | 2% |
| TYPE OF INFECTION | Other |
| FREQUENCY OF INFECTION | 2% |

TIA-transient ischaemic attack.* Those with stroke subtype repeated. †First month.

FIG. 1G

PREVENTION OF INFECTION

CROSS-REFERENCE TO RELATED APPLICATIONS

This application claims the benefit of U.S. Provisional Patent Application Ser. No. 61/516,227, filed Mar. 31, 2011, the disclosure of which is incorporated herein in its entirety by reference thereto.

BACKGROUND OF THE INVENTION

1. Field of Invention

This invention relates to compounds and methods for the prevention and/or treatment of infection after stroke or central nervous system (CNS) injury.

2. Description of Related Art

The invention discloses agents for the prevention of infections after ischemic stroke or other CNS injury in order to reduce lethality and morbidity. Infections are severe complications, which commonly occur in the early phase after stroke and have a negative prognostic influence. The agents employed according to the invention, in pharmaceutical preparations, constitute substances which are glucocorticoid receptor antagonists. The invention moreover refers to agents for therapy after stroke, this approach having the aim to prevent and/or treat infections after stroke.

The stroke patient, besides the direct consequences of stroke, which may range from transitory to permanent neurological failures or death in the acute and early remission phase, is particularly endangered by infections. Infections, especially pneumonias, constitute the major cause of lethality in stroke (Henon et al. 1995, Katzan et al. 2003, List of References following the examples). Thus, 21-65% of acute stroke patients develop infections and 10-22% develop pneumonias (Davenport et al. 1996, Castillo et al. 1998, Johnston et al. 1998, Grau et al. 1999, Georgilis et al. 1999, Langhorne et al. 2000). The comparison with the incidence of nosocomial infections occurring in an average of 7-10% of all patients (Bucher 2000) and about 3% of postoperative patients (Smyth & Emmerson 2000), particularly underlines the very high frequency of infections in acute stroke patients. In a systematic investigation, it was shown, that the risk of infection is highest at the first and second day after stroke (Grau et al. 1999). See FIG. 1.

There is increasing evidence that normally well balanced brain-immune interactions become dysregulated after stroke. CNS injury, such as stroke, induces immunodepression thought to be mediated largely by elevated circulating cortisol, either as a stress response or related primarily to the neural pathways impaired by the stroke itself. Elevated concentrations of cortisol in patients with acute stroke are associated with more severe stroke, larger infarct volume and worse outcome. Thus, there is a need for methods for the prevention and/or treatment of infection after stroke. The prevention of stroke-induced infections by means of, for example, a glucocorticoid receptor antagonist as a means of a preventive, anti-infective therapy constitutes a novel approach. The present invention relates to the blocking of this early rise of cortisol by the administration of such a glucocorticoid receptor antagonist. It is expected that a short treatment with a glucocorticoid receptor antagonist after stroke will diminish or prevent the occurrence of infections and will also have a positive impact on infarct severity and long term outcome.

All references cited herein are incorporated herein by reference in their entireties.

BRIEF SUMMARY OF THE INVENTION

The invention provides a method for treating or preventing infection after ischemic stroke wherein said method comprises administering to a patient in need of such therapy at least one glucocorticoid receptor antagonist in a therapeutically effective amount.

The invention provides a method wherein the at least one glucocorticoid receptor antagonist is in a pharmaceutical preparation.

The invention provides a method wherein the glucocorticoid receptor antagonist is selected from the group consisting of ORG 34517, 11-(substituted phenyl)-estra-4,9-diene derivatives, and 11-(substituted phenyl)-estra-4,9-diene derivatives of formula I

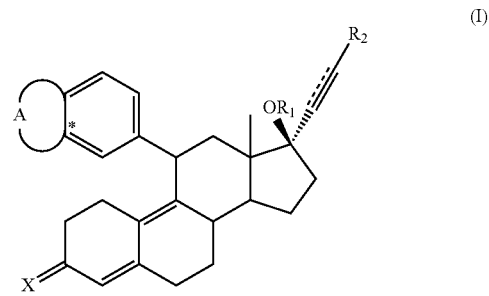

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H$_2$OH), O, and NOH; and the interrupted line represents an optional bond.

The invention provides a method of treating or preventing infection secondary to CNS injury in a patient in need thereof, comprising administering at least one GCR antagonist in a therapeutically effective amount.

The invention provides a method wherein the CNS injury is selected from the group consisting of stroke, neuronal damage resulting from head trauma, epilepsy, pain, migraine, a mood disorder, schizophrenia, a neurodegenerative disorder, depression, anxiety, a psychosis, hypertension or cardiac arrhythmia, and combinations thereof.

The invention provides a kit for treating or preventing infection after ischemic stroke comprising: (a) a pharmaceutical composition comprising at least one glucocorticoid receptor antagonist in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing infection after ischemic stroke.

The invention provides a product of manufacture for treating or preventing infection after ischemic stroke comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for use of the pharmaceutical composition for treating or preventing infection after ischemic stroke.

The invention provides a method for reducing infarct severity and improving long term outcome after ischemic stroke wherein said method comprises administering, to a patient in need of such therapy, at least one glucocorticoid receptor antagonist in a therapeutically effective amount.

The invention provides a method wherein the at least one glucocorticoid receptor antagonist is in a pharmaceutical preparation.

The invention provides a method wherein the glucocorticoid receptor antagonist is selected from the group consisting of ORG 34517, 11-(substituted phenyl)-estra-4,9-diene derivatives, and 11-(substituted phenyl)-estra-4,9-diene derivatives of formula I

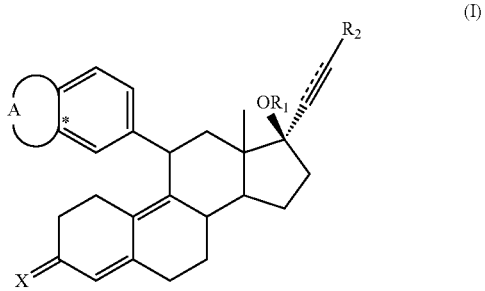

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from ($H_2OH$), O, and NOH; and the interrupted line represents an optional bond.

The invention provides a method of treating or preventing infection secondary to CNS injury in a patient in need thereof, comprising administering at least one GCR antagonist in a therapeutically effective amount.

The invention provides a method for improving long term outcome secondary to CNS injury in a patient in need thereof, comprising administering at least one GCR antagonist.

The invention provides a method wherein the CNS injury is selected from the group consisting of stroke, neuronal damage resulting from head trauma, epilepsy, pain, migraine, a mood disorder, schizophrenia, a neurodegenerative disorder, depression, anxiety, a psychosis, hypertension or cardiac arrhythmia, and combinations thereof.

The invention provides a kit for reducing infarct severity and improving long term outcome after ischemic stroke comprising: (a) a pharmaceutical composition comprising at least one GCR antagonist; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing infection after ischemic stroke.

The invention provides a product of manufacture for reducing infarct severity and improving long term outcome after ischemic stroke comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for use of the pharmaceutical composition for treating or preventing infection after ischemic stroke.

BRIEF DESCRIPTION OF SEVERAL VIEWS OF THE DRAWINGS

The invention will be described in conjunction with the following drawings in which like reference numerals designate like elements and wherein:

FIG. 1A, FIG. 1B, FIG. 1C, FIG. 1D, FIG. 1E, FIG. 1F and FIG. 1G comprise a table showing several studies which have reported an increased infection rate after stroke.

DETAILED DESCRIPTION OF THE INVENTION

The invention is directed to the use of, for example, a glucocorticoid receptor antagonist for preventive anti-infective therapy after, for example, stroke, and for the production of medicines and/or pharmaceutical preparations for preventive anti-infective therapy after stroke. Respiratory tract infections ranged from 1-33% after stroke and urinary tract infections ranged from 2-27%. These infections have a high impact on morbidity and mortality. The 30-day-mortality rate in patients with pneumonia is 27% while the mortality rate is 4% in stroke patients without pneumonia. Also, the disability in stroke patients with pneumonia is higher than in patients without, resulting in increased medical costs and a lower quality of life. It is ethically and medically preferred to prevent or treat the post-stroke infections. Presently, trials of antibiotics for the prevention and treatment of post-stroke infections are underway.

The term "early preventive, anti-infective therapy after stroke" means that the treatment is started within 72 hours after the stroke event.

As used herein, the term "effective amount" refers to the amount of a therapy that is sufficient to result in the prevention of the development, recurrence, or onset of a disease or condition, such as infection subsequent to stroke, and one or more symptoms thereof, to enhance or improve the prophylactic effect(s) of another therapy, reduce the severity, the duration of a disease or condition, such as infection subsequent to stroke, ameliorate one or more symptoms of a disease or condition, such as infection subsequent to stroke, prevent the advancement of a disease or condition, such as infection subsequent to stroke, cause regression of a disease or condition, such as infection subsequent to stroke, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, such as infection subsequent to stroke or a symptom thereof in a subject resulting from the administration of a therapy (e.g., a prophylactic or therapeutic agent), or a combination of therapies (e.g., a combination of prophylactic or therapeutic agents).

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the terms "therapies" and "therapy" can refer to any method(s), composition(s), and/or agent(s) that can be used in the prevention, treatment and/or management of a disease or condition, such as infection subsequent to stroke, or one or more symptoms thereof.

As used herein, the terms "treat," "treatment," and "treating" in the context of the administration of a therapy to a subject refer to the reduction or inhibition of the progression and/or duration of a disease or condition, such as infection subsequent to stroke, the reduction or amelioration of the severity of a disease or condition, such as infection subsequent to stroke, and/or the amelioration of one or more symptoms thereof resulting from the administration of one or more therapies.

Stroke

Stroke (also referred to herein as acute stroke, ischemic stroke and/or cerebrovascular ischemia) is often cited as the third most common cause of death in the industrial world, ranking behind ischemic heart disease and cancer. Strokes are responsible for about 300,000 deaths annually in the United States and are a leading cause of hospital admissions and long-term disabilities. Accordingly, the socioeconomic impact of stroke and its attendant burden on society is practically immeasurable.

"Stroke" is defined by the World Health Organization as a rapidly developing clinical sign of focal or global disturbance of cerebral function with symptoms lasting at least 24 hours. Strokes are also implicated in deaths where there is no apparent cause other than an effect of vascular origin.

Strokes are typically caused by blockages or occlusions of the blood vessels to the brain or within the brain. With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

A subject having a stroke is so diagnosed by symptoms experienced and/or by a physical examination including interventional and non-interventional diagnostic tools such as CT and MR imaging. The methods of the invention are advantageous for the treatment of various clinical presentations of stroke subjects. A subject having a stroke may present with one or more of the following symptoms: paralysis, weakness, decreased sensation and/or vision, numbness, tingling, aphasia (e.g., inability to speak or slurred speech, difficulty reading or writing), agnosia (i.e., inability to recognize or identify sensory stimuli), loss of memory, co-ordination difficulties, lethargy, sleepiness or unconsciousness, lack of bladder or bowel control and cognitive decline (e.g., dementia, limited attention span, inability to concentrate). Using medical imaging techniques, it may be possible to identify a subject having a stroke as one having an infarct or one having hemorrhage in the brain.

The treatment and/or prevention of infection after stroke can be for patients who have experienced a stroke or can be a prophylactic treatment. Short term prophylactic treatment is indicated for subjects having surgical or diagnostic procedures which risk release of emboli, lowering of blood pressure or decrease in blood flow to the brain, to reduce the injury due to any ischemic event that occurs as a consequence of the procedure. Longer term or chronic prophylactic treatment is indicated for subjects having cardiac conditions that may lead to decreased blood flow to the brain, or conditions directly affecting brain vasculature. If prophylactic, then the treatment is for subjects having an abnormally elevated risk of an ischemic stroke, as described above. If the subject has experienced a stroke, then the treatment can include acute treatment. Acute treatment for prevention of infection after stroke in a patient means administration of an agent of the invention at the onset of symptoms of the condition or within 48 hours of the onset, preferably within 24 hours, more preferably within 12 hours, more preferably within 6 hours, and even more preferably within 3 hours of the onset of symptoms of the condition.

An important embodiment of the invention is treatment of a subject with an abnormally elevated risk of an ischemic stroke. As used herein, subjects having an abnormally elevated risk of an ischemic stroke is a category determined according to conventional medical practice; such subjects may also be identified in conventional medical practice as having known risk factors for stroke or having increased risk of cerebrovascular events. Subjects having an abnormally elevated risk of an ischemic stroke includes, for example, individuals undergoing surgical or diagnostic procedures which risk release of emboli, lowering of blood pressure or decrease in blood flow to the brain, such as carotid endarterectomy, brain angiography, neurosurgical procedures in which blood vessels are compressed or occluded, cardiac catheterization, angioplasty, including balloon angioplasty, coronary by-pass surgery, or similar procedures.

Glucocorticoid Receptor Antagonists

Glucocorticoid receptor antagonists bind to the receptor and prevent glucocorticoid receptor agonists from binding and eliciting glucocorticoid receptor mediated events, including transcription. These antagonists may be non-selective. RU486 is an example of a non-selective glucocorticoid receptor antagonist; its primary binding site is to progesterone receptors, but has cross-reactivity, with lesser affinity, to other steroid hormone receptors, including the glucocorticoid receptor. Other compounds having high glucocorticoid receptor binding affinity and, in addition, high in vivo anti-glucocorticoid activity, while having, for example, low androgenic and progestagenic activities are disclosed in U.S. Pat. No. 6,011,025, incorporated herein by reference in its entirety. ORG 34517 is an example of a compound with high glucocorticoid receptor binding affinity while having low androgenic and progestagenic activities.

It has been found that 11-(substituted phenyl)-estra-4,9-diene derivatives of formula I

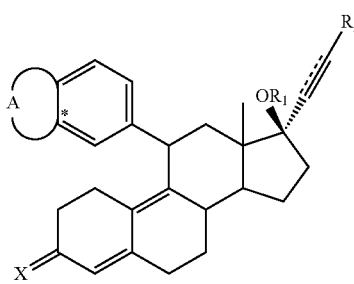

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from ($H_2$OH), O, and NOH; and the interrupted line represents an optional bond, show specific and high glucocorticoid receptor binding affinity and are highly active in vivo showing predominant anti-glucocorticoid activity.

The compounds lack appreciable affinity for mineralocorticoid, progesterone, estrogen and androgen receptors, indicating a clean side effect profile.

The 11-(substituted phenyl)-estra-4,9-diene derivatives of the invention can be used in the prevention and treatment of glucocorticoid dependent diseases or symptoms, like Cushing syndrome, diabetes, glaucoma, sleep disturbances, depression, anxiety, atherosclerosis, hypertension, adiposity, osteoporosis and withdrawal symptoms from narcotics and their mixtures.

Preferred compounds according to this invention are 11-(substituted phenyl) estra-4,9-diene derivatives, wherein the heteroatom(s) are (is) O, the 5- or 6-membered ring being optionally substituted with one or more fluorine atoms; R1 is H; and X is O or NOH. More preferred compounds are 11-(substituted phenyl) estra-4,9-diene derivatives wherein A is a residue of a 5-membered ring. Particularly preferred are 11-(substituted phenyl) estra-4,9-diene derivatives wherein A contains 2 heteroatoms being O.

Especially preferred are 11-(substituted phenyl) estra-4,9-diene derivatives wherein R2 is methyl and the interrupted line represents a bond.

The most preferred compound is (11β,17β)-11-(1,3-benzodioxol-5-yl)-17-hydroxy-17-(1-propynyl) estra-4,9-dien-3-one (ORG 34517).

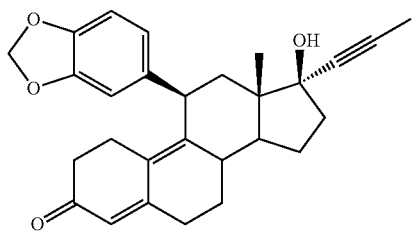

ORG 34517

The term halogen means a fluorine, chlorine, bromine or iodine atom. Fluorine is the preferred halogen in ring A and when R2 is halogen, chlorine is preferred.

The terms (1-4C)alkyl and (1-8C)alkyl, as used in the definitions of R1 and R2, respectively, mean alkyl groups having 1-4 and 1-8 carbon atoms, respectively, for example methyl, ethyl, propyl, isopropyl, butyl, sec-butyl, tert-butyl, pentyl, neopentyl, hexyl, octyl.

The 11-(substituted phenyl)-estra-4,9-diene derivatives according to the present invention can be prepared by a process wherein a compound of formula II

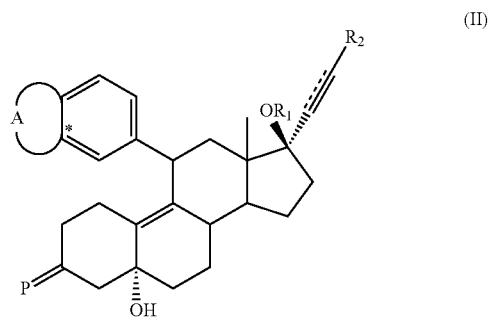

(II)

wherein A, R2 and the interrupted line have the meanings as previously defined, R1 is H, and P is a protected keto-group, is dehydrated and deprotected, after which the 17β-OH is optionally esterified by reaction with an appropriate carboxylic acid to give a derivative wherein R1 is 1-oxo(1-4C)alkyl, and optionally the 3-oxo group is converted into the corresponding 3-hydroxy- or 3-oxime derivative. The 3-oxo group can be reduced to form the 3-hydroxy-derivative by using a suitable reducing agent, such as sodium borohydride. The 3-oxime derivatives can be prepared by hydroxylamine treatment in a suitable solvent, like pyridine.

The derivatives of formula II may be prepared according to well known methods described and used for the preparation of steroids.

A suitable process for the preparation of derivatives of formula II starts from estra-4,9-diene-3,17-dione. Selective reduction of the 17-keto group to 17β-OH, 17α-H, e.g. with sodium borohydride, followed by protection of the 3-keto group, e.g., by ketalisation with ethyleneglycol, triethylorthoformate and p-toluenesulfonic acid, and oxidation of the 17-hydroxy group, e.g., with pyridinium chlorochromate, provides the 3-ketoprotected estra-5(10),9(11)-diene-3,17-dione. Alkynylation at the 17-position (yielding a 17α-alkynyl,17β-OH derivative), followed by epoxidation of the 5(10) double bond, e.g., with hydrogen peroxide, trifluoroacetophenone, and pyridine in dichloromethane according to the method as disclosed in European patent application EP 0 298 020, provides the 3-ketoprotected 5α,10α-epoxy-17α-alkynyl-17β-hydroxy-estr-9(11)-ene-3-one.

Subsequently, compounds of formula II are formed from this epoxide derivative, for example by reaction with an organometallic compound of the formula

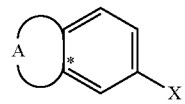

wherein X is a (alkali)metal, like lithium, or a magnesiumhalide, preferably magnesium bromide.

Suitable protective groups and methods to remove these groups are known in the art, for example from T. W. Green: Protective Groups in Organic Synthesis (Wiley, N.Y., 1981). Particularly suitable protective groups for the protection of keto groups are acetals, e.g., 1,2-ethylene ketal.

The specificity of ORG 34517 for GR blockade, without significant cross-binding to other related steroidal hormone receptors (such as those for estrogen and progesterone), eliminates the likelihood of significant toxicities and side effects. Indeed, none were identified in all the substantial phase I and phase II clinical trials that already have been performed with the compound. Because the drug is envisioned as being used in limited dosing over time, coordinated with the intermittent dosing strategies typical for chemotherapeutic agents, the GR blockade also would not lead to significant alteration of HPA-axis functioning, with rapid restitution of the HPA-axis to baseline following dosing.

Formulations

The compounds of the invention may be administered enterally or parenterally. Mixed with pharmaceutically suitable auxiliaries, e.g., as described in the standard reference, Gennaro et al., Remington's Pharmaceutical Sciences, 2005. The compounds may be compressed into solid dosage units, such as pills, tablets, or be processed into capsules or suppositories. By means of pharmaceutically suitable liquids the compounds can also be applied in the form of a solution, suspension, emulsion, e.g., for use as an injection preparation or eye drops, or as a spray, e.g., for use as a nasal spray.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Dosage forms of the compositions of the present invention can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present invention, the combination of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like.

The dose administered must be carefully adjusted according to age, weight and condition of the patient, as well as the route of administration, dosage form and regimen and the desired result.

The pharmaceutical compositions of the invention may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

One embodiment of this invention includes methods of treating, preventing, or diagnosing a particular disease or condition by administering the disclosed nanoparticles, composite nanoparticles, nanosuspension, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

"Nanoparticles" are solid particles of an average particle diameter of, for example, less than about 1 micron (micrometer). One micron is 1,000 nanometers (nm).

"Stabilized" nanoparticles are nanoparticles coated with a stabilizing material and having a reduced tendency for aggregation and loss of dispersion with respect to nanoparticles of the compound of the invention without a stabilizing coating.

A nano-spray is a spray containing nanoparticles or a spray that produces nanoparticles. A nanodispersion is a dispersion containing nanoparticles. A nanosuspension is a suspension containing nanoparticles.

The liquid formulations useful herein may comprise a solvent, solution, suspension, microsuspension, nanosuspension, emulsion, microemulsion, gel or even a melt containing the active component or components. In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid.

Pharmaceutical compositions of the present invention can include nanoparticles, composite nanoparticles, nanosuspension, or nanocapsules of the present invention.

In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Packaging/Treatment Kits

The present invention relates to a kit for conveniently and effectively carrying out the methods in accordance with the present invention. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose.; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists two or more separate compartments: Am dosage of this invention, and PM dosage of this invention, or mid-day dosage of this invention. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside.

In one aspect, blister packaging comprises at least two components (e.g., is a multi-ingredient combination of drugs of the invention): a thermoformed "blister" which houses the product (e.g., a pharmaceutical combination of the invention), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, Ill.) using regular heat seal tooling. This alternative aspect, using heat seal tooling, can seal common types of thermoformed packaging.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

In one aspect, laminated aluminum foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual push-through blister packs/packettes are used, e.g., using hard temper aluminum (e.g., alufoil) lidding material. In one aspect, hermetically-sealed high barrier aluminum (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

CNS Injury

Conditions suitable for treatment according to this invention include, for example, seizure disorders, pain syndromes, neurodegenerative diseases (including motor-neuron diseases, myelopathies, radiculopathies, and disorders of the sympathetic nervous system), dementias, cerebrovascular conditions, movement disorders, brain trauma, cranial nerve disorders, neuropsychiatric disorders, and other disease neuropathies (including viral associated neuropathies, diabetes associated neuropathies, Guillian-Barre syndrome, dysproteinemias, transthyretin-induced neuropathies, and carpal tunnel syndrome).

As used herein, seizure disorders include complex partial seizures, simple partial seizures, partial seizures with secondary generalization, generalized seizures (including absence, grand mal (tonic clonic), status epilepticus, tonic, atonic, myoclonic), neonatal and infantile spasms, drug-induced seizures, trauma-induced seizures, and febrile seizures, and additional specific epilepsy syndromes such as juvenile myoclonic epilepsy, Lennox-Gastaut, mesial temporal lobe epilepsy, nocturnal frontal lobe epilepsy, progressive epilepsy with mental retardation, and progressive myoclonic epilepsy, as well as seizures associated with CNS mass lesions.

Pain syndromes include, for example, headaches (e.g., migraine, tension, and cluster), acute pain, chronic pain, neuropathic pain, nociceptive pain, central pain and inflammatory pain, drug-induced neuropathic pain, causalgia, complex regional pain syndrome types I and II, and reflex sympathetic dystrophy (RSDS).

Neurodegenerative diseases include Alzheimer's disease, Parkinson's Disease, multiple sclerosis, Huntington's Disease, ALS, spinal muscular atrophy, muscular dystrophies prion-related diseases, cerebellar ataxia, Friedrich's ataxia, SCA, Wilson's disease, RP, Gullian Bane syndrome, Adrenoleukodystrophy, Menke's Sx, cerebral autosomal dominant arteriopathy with subcortical infarcts (CADASIL), Charcot Marie Tooth diseases, neurofibromatosis, von-Hippel Lindau, Fragile X, spastic paraplegia, tuberous sclerosis complex, Wardenburg syndrome, spinal motor atrophies, Tay-Sach's, Sandoff disease, familial spastic paraplegia, myelopathies, radiculopathies, encephalopathies associated with trauma, radiation, drugs and infection, and disorders of the sympathetic nervous system (e.g., Shy Drager (familial dysautonomia), diabetic neuropathy, drug-induced and alcoholic neuropathy).

Dementias include Alzheimer's disease, Parkinson's disease, Pick's disease, fronto-temporal dementia, vascular dementia, normal pressure hydrocephalus, Huntington's disease, and MCI.

Cerebrovascular conditions amenable to treatment according to the present invention include cerebrovascular disease and strokes (e.g., thrombotic, embolic, thromboembolic, hemorrhagic [including AVM and berry aneurysms], venoconstrictive, and venous).

Included in movement disorders are Parkinson's disease, dystonias, benign essential tremor, tardive dystonia, tardive dyskinesia, and Tourette's syndrome.

Brain trauma as used herein includes traumatic brain and spinal cord injuries as well as brain injuries from radiation.

Cranial nerve disorders include trigeminal neuropathy, trigeminal neuralgia, Menier's syndrome, glossopharangela neuralgia, dysphagia, dysphonia, cranial nerve palsies and Bell's palsy.

Neuropsychiatric disorders include panic syndrome, general anxiety disorder, phobic syndromes of all types, mania, manic depressive illness, hypomania, unipolar depression, depression, stress disorders, PTSD, somatoform disorders, personality disorders, psychosis, and schizophrenia), and drug dependence/addiction (e.g., alcohol, psychostimulants (e.g., crack, cocaine, speed, meth), opioids, and nicotine), and drug-induced psychiatric disorders.

Other disease neuropathies that may be treated with the compositions and methods described herein include Guillian-Barre, diabetes associated neuropathies, dysproteinemias, transthyretin-induced neuropathies, neuropathy associated with HIV, herpes viruses (including herpes zoster) or other viral infection, neuropathy associated with Lyme disease, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy, post-meningitis syndrome, post-polio syndrome, prion diseases, and radiation associated neuropathic syndromes.

Other diseases amenable to treatment with the present invention include fatigue syndromes (e.g., chronic fatigue syndrome and fibromyalgia), ataxic syndromes, olivopontoicerebellar degeneration, striatonigral degeneration, and axonic brain damage.

The present invention is particularly useful in the treatment of neuropsychiatric disorders such as depression, agitation, anxiety, seizure disorders such as grand mal seizures, status epilepticus, migraine pain treatment and prophylaxis, Alzheimer's disease, Parkinson's disease, and traumatic brain and spinal cord injury.

Also, the higher doses enabled by the present invention are expected to be of particular importance for dementias including Alzheimer's disease, Parkinson's disease, and vascular dementia, pain syndromes, including headaches and migraines, seizure disorders, movement disorders, and brain trauma.

Furthermore, the ease of use and convenience of a dosage form provided developed to be delivered at once per day or less frequent administration at a therapeutically effective quantity from the onset of therapy is of value in the treatment of dementias including Alzheimer's disease and Parkinson's disease, seizure disorders, pain syndromes, and cerebrovascular conditions.

Formulations for Alternate Specific Routes of Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The GCR antagonist may also be delivered in an aerosol spray preparation from a pressurized pack, a nebulizer or from a dry powder inhaler. Suitable propellants that can be used in a nebulizer include, for example, dichlorodifluoromethane, trichlorofluoromethane, dichlorotetrafluoroethane and carbon dioxide. The dosage can be determined by providing a valve to deliver a regulated amount of the compound in the case of a pressurized aerosol.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

While the invention has been described in detail herein, it will be apparent to one skilled in the art that various changes and modifications can be made therein without departing from the spirit and scope thereof.

What is claimed is:

1. A method for treating or preventing infection after ischemic stroke wherein said method comprises administering to a patient in need of such therapy at least one glucocorticoid receptor antagonist in a therapeutically effective amount.

2. The method, according to claim 1, wherein the at least one glucocorticoid receptor antagonist is in a pharmaceutical preparation.

3. The method of claim 1, wherein the glucocorticoid receptor antagonist is selected from the group consisting of ORG 34517, 11-(substituted phenyl)-estra-4,9-diene derivatives, and 11-(substituted phenyl)-estra-4,9-diene derivatives of formula I

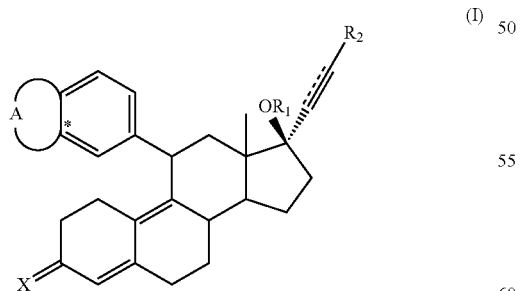

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from ($H_2$OH), O, and NOH; and the interrupted line represents an optional bond.

4. A method of treating or preventing infection secondary to central nervous system injury in a patient in need thereof, comprising administering at least one glucocorticoid receptor antagonist in a therapeutically effective amount.

5. The method of claim 4, wherein the CNS injury is selected from the group consisting of stroke, neuronal damage resulting from head trauma, epilepsy, pain, migraine, a mood disorder, schizophrenia, a neurodegenerative disorder, depression, anxiety, a psychosis, hypertension or cardiac arrhythmia, and combinations thereof.

6. A kit for treating or preventing infection after ischemic stroke comprising:
   (a) a pharmaceutical composition comprising at least one glucocorticoid receptor antagonist in a therapeutically effective amount; and
   (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing infection after ischemic stroke.

7. A product of manufacture for treating or preventing infection after ischemic stroke comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for use of the pharmaceutical composition for treating or preventing infection after ischemic stroke.

8. A method for reducing infarct severity and improving long term outcome after ischemic stroke wherein said method comprises administering, to a patient in need of such therapy, at least one glucocorticoid receptor antagonist in a therapeutically effective amount.

9. The method, according to claim 8, wherein the at least one glucocorticoid receptor antagonist is in a pharmaceutical preparation.

10. The method of claim 8, wherein the glucocorticoid receptor antagonist is selected from the group consisting of ORG 34517, 11-(substituted phenyl)-estra-4,9-diene derivatives, and 11-(substituted phenyl)-estra-4,9-diene derivatives of formula I

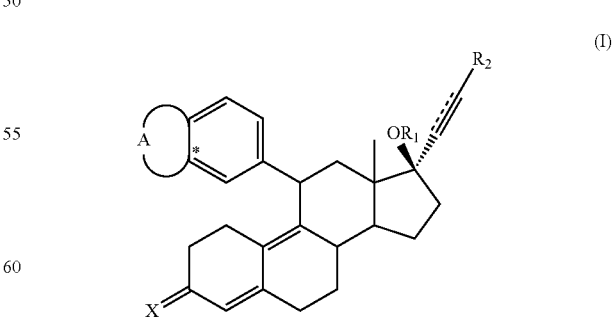

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H$_2$OH), O, and NOH; and the interrupted line represents an optional bond.

11. A method for improving long term outcome secondary to CNS injury in a patient in need thereof, comprising administering at least one GCR antagonist.

12. The method of claim 11, wherein the CNS injury is selected from the group consisting of stroke, neuronal damage resulting from head trauma, epilepsy, pain, migraine, a mood disorder, schizophrenia, a neurodegenerative disorder, depression, anxiety, a psychosis, hypertension or cardiac arrhythmia, and combinations thereof.

13. A kit for reducing infarct severity and improving long term outcome after ischemic stroke comprising:

(a) a pharmaceutical composition comprising at least one GCR antagonist; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition for treating or preventing infection after ischemic stroke.

14. A product of manufacture for reducing infarct severity and improving long term outcome after ischemic stroke comprising a blister package; a lidded blister; a blister card or packet; a clamshell; an intravenous (IV) package, IV packette or IV container; a tray or a shrink wrap comprising a pharmaceutical composition comprising at least one glucocorticoid receptor antagonist, and instructions for use of the pharmaceutical composition for treating or preventing infection after ischemic stroke.

* * * * *